United States Patent [19]

Giuffre et al.

[11] 4,288,382

[45] Sep. 8, 1981

[54] REVERSIBLE ADDUCTS OF ISOCYANATES WITH BORON COMPOUNDS

[75] Inventors: Luigi Giuffre, Milan, Italy; Placido M. Spaziante, Lugano, Switzerland

[73] Assignee: Vertac, Inc., Memphis, Tenn.

[21] Appl. No.: 83,400

[22] Filed: Oct. 10, 1979

[51] Int. Cl.$^3$ ........................................ C07C 119/042
[52] U.S. Cl. ........................... 260/453 A; 260/453 SP
[58] Field of Search ...................... 260/453 A, 453 SP

[56] References Cited

U.S. PATENT DOCUMENTS

| | | | |
|---|---|---|---|
| 3,734,941 | 5/1973 | Sydor | 260/453 P |
| 3,755,401 | 8/1973 | Vestal | 260/453 A |
| 4,003,938 | 1/1977 | Koenig et al. | 260/453 P |

Primary Examiner—Alan L. Rotman
Assistant Examiner—Robert C. Whittenbaugh
Attorney, Agent, or Firm—Hammond & Littell, Weissenberger and Muserlian

[57] ABSTRACT

Adducts of low boiling isocyanates with boron compounds selected from the group consisting of polyol borates and metaboric acid which decompose on heating to give the low boiling isocyanates as a condensible vapor; as well as the method of making the adducts and the method of storing and transporting low boiling isocyanates employing said adducts.

20 Claims, No Drawings

REVERSIBLE ADDUCTS OF ISOCYANATES WITH BORON COMPOUNDS

BACKGROUND OF THE INVENTION

Methyl isocyanate, ethyl isocyanate and other low boiling isocyanates are difficult to store and transport due to their high vapor pressure, toxicity and flammability. Even such compounds as phenyl isocyanate and the isomeric tolyl isocyanates which boil at temperatures from 167° C. to about 200° C. present storage and transportation problems.

Many compounds are known to react with isocyanates through double bond addition to the N=C bond. Reaction with alcohols from N-methylcarbamoyl esters which are relatively stable compounds. The reaction of naphthyl isocyanate with phenols is a classic method of characterizing phenols.

It has been conventional practice to obtain low boiling isocyanates from the corresponding carbamoyl chloride by heating in an appropriate solvent inert to isocyanate while separating the hydrochloric acid from the gaseous isocyanate. A recent U.S. Pat. No. 4,082,787 makes a review of various processes.

U.S. Pat. No. 4,003,938 describes a method for obtaining low boiling isocyanates by decomposing the corresponding β-naphthyl carbamates at temperatures of from 150° C. to 500° C. This process, however, presents difficulties as the β-naphthyl carbamate is a solid at room temperature and the reaction requires a vacuum.

The low boiling isocyanates are considered to be alkyl isocyanates having from 1 to 10 carbon atoms, preferably from 1 to 4 carbon atoms, in the alkyl and alkenyl isocyanates having from 2 to 6 carbon atoms in the alkenyl. Such compounds have the boiling points given in Table I.

TABLE I

| Isocyanate | Boiling Point °C. |
|---|---|
| Methyl | 38–45 |
| Ethyl | 60 |
| Isopropyl | 74 |
| n-Propyl | 88 |
| Allyl | 88 |
| n-Butyl | 115 |
| t.-Butyl | 85 |
| CH$_3$—C(CH$_3$)$_2$—CH(CH$_3$)— | 58 (13 mm) |
| di-(n-propyl)-methyl | 40 (12 mm) |

U.S. Pat. No. 4,146,550 describes a process for preparation of aliphatic monoisocyanates by reacting the corresponding carbamic acid chloride with sulfuric acid or sulfonic acid amides, certain activated phenols containing electrophilic groups and certain substituted urethanes and then subjecting the reaction product to pyrolysis at temperatures of from 100° C. to 250° C. to recover the aliphatic isocyanates. This process requires the use of a solvent, such as chlorobenzene, and the aliphatic isocyanate and solvent are recovered as a mixture which must be carefully redistilled to recover the aliphatic isocyanate.

OBJECTS OF THE INVENTION

An object of the present invention is to develop an adduct of low boiling isocyanates which form liquids or solids which readily undergo a reversible reaction on heating to release the low boiling isocyanate as a gas.

Another object of the present invention is to obtain an adduct of (1) an isocyanate having the formula:

R—N=C=O wherein R is a member selected from the group consisting of alkyl having from 1 to 10 carbon atoms and alkenyl having 2 to 6 carbon atoms with (2) a boron compound having at least one free =B—OH group selected from the group consisting of (a) polyol borates essentially free of alcoholic hydroxyl groups prepared from boric acid and polyols having at least two alcoholic hydroxyl groups selected from the group consisting of (i) compounds having the formula

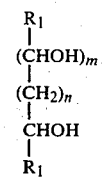

wherein R$_1$ is a member selected from the group consisting of hydrogen, lower alkyl, and hydrocarbon aryl, n is 0 or an integer from 1 to 4, and m is 0 or an integer from 1 to 5, (ii) pentaerythritol, (iii) lower alkyl ethers of (i) or (ii), and (iv) lower alkanoic acid esters of (i) or (ii), and (b) metaboric acid A further object of the present invention is the development of a process for storing and transporting an isocyanate having the formula:

R—N=C=O wherein R is a member selected from the group consisting of alkyl having from 1 to 10 carbon atoms and alkenyl having from 2 to 6 carbon atoms, consisting of the steps of reacting a carbonyl group containing compound selected from the group consisting of an isocyanate having the formula

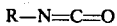

R—N=C=O wherein R is a member selected from the group consisting of alkyl having from 1 to 10 carbon atoms and alkenyl having 2 to 6 carbon atoms, and a carbamoyl chloride having the formula

R—NH—C(=O)—Cl wherein R has the above assigned values, with a boron compound having at least one free =B—OH group selected from the group consisting of (a) polyol borates essentially free of alcoholic hydroxyl groups prepared from boric acid and polyols having at least two alcoholic hydroxyl groups selected from the group consisting of (i) compounds having the formula

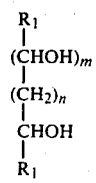

wherein $R_1$ is a member selected from the group consisting of hydrogen, lower alkyl, and hydrocarbon aryl, n is 0 or an integer from 1 to 4, and m is 0 or an integer from 1 to 5, (ii) pentaerythritol, (iii) lower alkyl ethers of (i) and (ii) and (iv) lower alkanoic acid esters of (i) or (ii), and (b) metaboric acid, either in the presence or absence of a solvent inert to isocyanate, to form an adduct, maintaining said adduct at temperatures below the decomposition temperature for the time desired, and heating said adduct to decompose the same with evolution of said isocyanate as a vapor.

These and other objects of the invention will become more apparent as the description thereof proceeds.

DESCRIPTION OF THE INVENTION

The above objects have been accomplished by the present discovery of adducts of low boiling isocyanates with boron compounds selected from the group consisting of polyol borates and metaboric acid which decompose on heating to give the isocyanates as a condensible vapor; as well as the method of making the adducts and the method of storing and transporting low boiling isocyanates employing said adducts.

In addition, the present invention relates to a process for storing and transporting an isocyanate having the formula:

$$R-N=C=O$$

wherein R is a member selected from the group consisting of alkyl having from 1 to 10 carbon atoms and alkenyl having from 2 to 6 carbon atoms, consisting of the steps of reacting a carbonyl group containing compound selected from the group consisting of an isocyanate having the formula $$R-N=C=O$$

wherein R is a member selected from the group consisting of alkyl having from 1 to 10 carbon atoms and alkenyl having 2 to 6 carbon atoms, and a carbamoyl chloride having the formula $$R-NH-\overset{O}{\underset{\|}{C}}-Cl$$

wherein R has the above assigned values, with a boron compound having at least one free $=B-OH$ group selected from the group consisting of (a) polyol borates essentially free of alcoholic hydroxyl groups prepared from boric acid and polyols having at least two alcoholic hydroxyl groups selected from the group consisting of (i) compounds having the formula $$\begin{array}{c} R_1 \\ | \\ (CHOH)_m \\ | \\ (CH_2)_n \\ | \\ CHOH \\ | \\ R_1 \end{array}$$

wherein $R_1$ is a member selected from the group consisting of hydrogen, lower alkyl and hydrocarbon aryl, n is 0 or an integer from 1 to 4, and m is 0 or an integer from 1 to 5, (ii) pentaerythritol, (iii) lower alkyl ethers of (i) or (ii), and (iv) lower alkanoic acid esters of (i) or (ii), and (b) metaboric acid, either in the presence or absence of a solvent inert to isocyanate, to form an adduct, maintaining said adduct at temperatures below the decomposition temperature for the time desired, and heating said adduct to decompose the same with evolution of said isocyanate as a vapor. This isocyanate vapor may be used as such or said isocyanate vapor can be condensed and said isocyanate recovered. The boron compound remaining can be recycled to form further adduct.

The boron compounds having at least one free $=B-OH$ group have been found to be excellent carriers for low boiling isocyanates, particularly those of the formula:

$$R-N=C=O$$

wherein R is a member selected from the group consisting of alkyl having from 1 to 10, preferably from 1 to 4, carbon atoms and alkenyl having from 2 to 6, preferably 3 to 4, carbon atoms, such as methyl isocyanate (MIC), boiling at 38° C. to 45° C. depending on purity, ethyl isocyanate, n-propyl isocyanate, isopropyl isocyanate, n-butyl isocyanate, isobutyl isocyanate, t.-butyl isocyanate, 2-methylbutyl isocyanate, pentyl isocyanate, neopentyl isocyanate, n-hexyl isocyanate, 1-methyl-2,2-dimethyl-propyl isocyanate, 1-propyl-butyl isocyanate, n-octyl isocyanate, n-decyl isocyanate, vinyl isocyanate, allyl isocyanate, isopropenyl isocyanate, 1,1-dimethyl-allyl isocyanate, etc. The preferred isocyanate employed, due to its use in organic synthesis, is methyl isocyanate.

The low boiling isocyanate or the corresponding carbamoyl chloride is reacted with said boron compound having at least one $=B-OH$ group preferably in about the stoichiometric amounts although the molar ratio of carbonyl group containing compound to $=B-OH$ can be from 1:1 to 1:10. The reaction, especially with the metaborate is conducted in an inert organic solvent to have the adduct in solution or slurry form for easy handling.

It is also part of the present invention to employ freshly prepared isocyanate or carbamoyl chloride from the reaction of phosgene with an amine according to the reactions:

$$R-NH_2 + O=CCl_2 \longrightarrow R-NH-\overset{O}{\underset{\|}{C}}-Cl + HCl$$

$$R-NH-\overset{O}{\underset{\|}{C}}-Cl \rightleftarrows R-N=C=O + HCl$$

$$R-N=C=O + 2HCl \rightleftarrows R-NHCCl + HCl$$
$$\phantom{R-N=C=O + 2HCl \rightleftarrows R-NH}\overset{O}{\underset{\|}{\phantom{C}}}\phantom{Cl + HCl}$$

Each of the above reactions are equilibrium reactions and at higher temperatures the production of $R-N=C=O$ is encouraged.

The gaseous reactants phosgene and the low boiling amine are mixed at elevated temperatures and then immediately contacted with a solution of the boron compound having at least one free $=B-OH$ group, such as metaboric acid in sulfolane or polyl borate in dioxane, at temperatures of from 25° C. to 125° C., where the adduct is formed and HCl vapors pass off.

The reaction of the isocyanate of the formula:

$$R-N=C=O$$

or the carbamoyl chloride of the formula

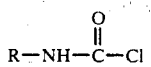

wherein R has the above-noted significance with metaboric acid or polyol borates occurs at temperatures of from above the freezing point of any solvent employed or the solidification point of said boron compound to below the decomposition point of the adduct formed, more preferably from $-5°$ C. to $125°$ C. most preferably from $30°$ C. to $100°$ C. The reaction is preferably conducted in the presence of an organic solvent inert to said isocyanate or said carbamoyl chloride and liquid at temperatures up to $100°$ C. These organic solvents can be chlorinated benzenes, cycloalkanes having 4 to 6 carbon atoms containing 1 to 2 hetero groups, such as oxygen, sulfur and sulfur dioxide, $C_{7-10}$ alkanes and chlorinated $C_{7-10}$ alkanes. Members of the above are chlorobenzene, dioxane, thiophene, sulfolane, benzine, chloroctane, etc. Depending on the solvent selection, either the boron compound may be soluble whereas its adduct with the isocyanate is substantially insoluble and a solid adduct can be recovered without the necessity of solvent distillation or the boron compound is soluble and the solution is utilized as the transporting and storage medium.

The polyol borates having at least one free $\equiv$B—OH group and essentially free of alcoholic hydroxyl groups are prepared by reacting boric acid and/or boric acid anhydride with a polyol having at least two alcoholic hydroxyl groups selected from the group consisting of (i) compounds having the formula

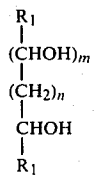

wherein R is a member selected from the group consisting of hydrogen, lower alkyl and hydrocarbon aryl, especially phenyl and toluyl, n is 0 or an integer from 1 to 4, m is 0 or an integer from 1 to 5, (ii) pentaerythritol, (iii) lower alkyl ethers of (i) or (ii) and (iv) lower alkanoic acid esters of (i) or (ii). The reaction between the glycol, boric acid and/or boric acid anhydride is conducted in an inert organic solvent, such as described above, at the reflux temperature while separating the azeotropically distilled water for a time sufficient to remove the required amount of water and recover a polyol borate free of alcoholic hydroxyl groups. The amount of reactants employed are such that the amount of acidic hydroxyl groups from the boric acid is in excess of the amount of alcoholic hydroxyl groups from the polyol.

Among the polyols having at least two alcoholic hydroxy groups of the above formula which can be utilized to prepare the polyol borate are, for example, ethylene glycol, propylene glycol, 1,3-butylene glycol, 1,2-butylene glycol, 1,4-butylene glycol, glycerol, glycerol monoacetate, methoxyglycerol, mannitol, pentaerythritol, etc. Ethylene glycol is preferred because of its availability and ease of handling.

The method to identify and measure the amount of $\equiv$B—OH present in the system consists in titrating the solution of the boric acid ester with a standard solution of sodium hydroxide using phenolphthalein as indicator or by potentiometric titration. The reaction involved is the following:

$$\equiv B-OH + NaOH \rightarrow \equiv B-ONa + H_2O$$

The alcoholic hydroxyl group is identified spectrometrically and is quantified by the water evolving from the reaction between boric acid and the free alcoholic hydroxyl groups.

The preparation of the polyol borates can be readily understood by the following reaction scheme, employing ethylene glycol as the polyol.

The ethylene glycol borates in a ratio of ethylene glycol to boron of from 3:2 to 1:1 are known compounds. The compounds with substantially a 1:1 ratio are described in U.S. Pat. Nos. 3,133,800 and 3,311,653. The boric acid esters of ethylene glycol (EGBE) may be either monomers (1:1 ratio) or polymers according to the following reactions:

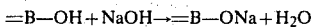

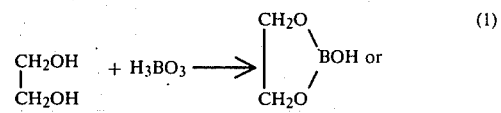

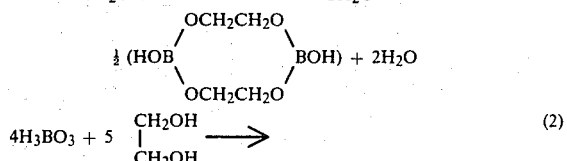

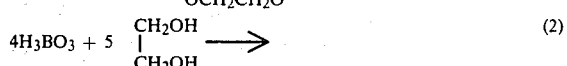

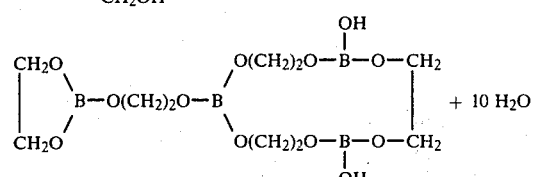

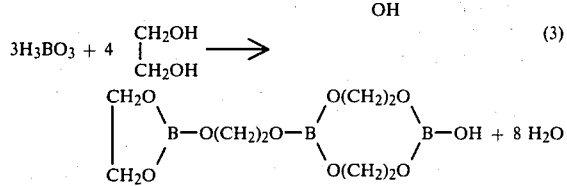

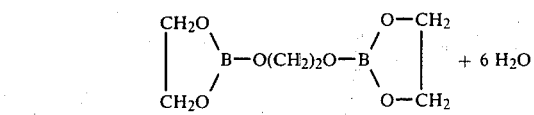

The most suitable ester is that of reaction (1) since the free —OH/B ratio is the highest. In each case the reaction to produce the EGBE is conducted so that the right amount of water relative to the desired free OH is removed.

The boric acid esters of ethylene glycol are prepared by reacting ethylene glycol, boric acid and/or boric acid anhydride in an inert organic solvent, such as described above, at the reflux temperature while separating the azeotropically distilled water vapor for a time sufficient to remove the required amount of water.

The metaboric acid is likewise a known compound. It reacts with the isocyanate as follows:

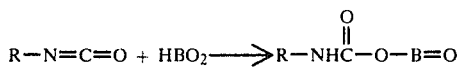

The reaction occurs either in the presence or absence of an inert organic solvent. Preferably a solvent is employed.

Any of the above adducts when heated to above 100° C., preferably to from 120° C. to 500° C., decompose to give a gaseous isocyanate and the solid metaboric acid or solution of metaboric acid or the solid to liquid polyol borate or solution of the polyol borate. It is thus possible to form the adduct, store the same at a temperature below the decomposition temperature and ship the same to the consumer. The consumer then heats the adduct to liberate gaseous isocyanate which is then processed as desired. The carrier boron compound, or its solution, can thus be recovered and returned for reuse to produce the adduct.

At any temperature, the adduct exists in an equilibrium with its constituents however the amount of isocyanate and boron compound present in the equilibrium mixture is barely detectable at temperatures below the decomposition temperature of the particular adduct. The decomposition temperature for any particular adduct can be readily determined experimentally.

Preferably the adduct is heated to substantially higher temperatures than the decomposition temperature, but below the decomposition temperature for the boron compound component thereof. When temperatures of from 220° C. to 250° C. are employed, from 70% to 75% of the low-boiling isocyanate can be recovered. The remainder of the adduct present together with the boron compound can be recycled to form futher adduct.

The following examples are illustrative of the practice of the invention without being limitative in any respect.

EXAMPLES

Preparation of EGBE

Ethylene glycol, boric acid and/or boric anhydride in dioxane were heated for one hour at dioxane reflux temperature. The dioxane/$H_2O$ azeotropic mixture was distilled afterwards until the boiling point of the distilling vapors was over 100° C. (pure dioxane). Water was then titrated in the distillate. If more concentrated EGBE solutions were desired, more dioxane was distilled. Three runs (A, B, C) were carried out, according to the stoichiometry in the following equations:

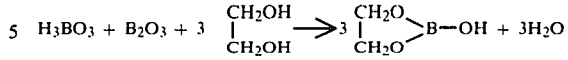

for Run A and

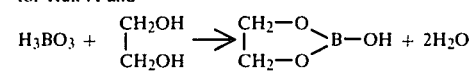

for Runs B and C.

The reaction conditions, material balances and results are given in Table II. In cases (A) and (B), the temperature in the distillation flask rose up to 200° C. at the end of the dioxane distillation. In case (C) a greater amount of dioxane was used and the temperature in the distillation flask was never greater than 110° C.

TABLE II

| | Preparation of Boric Acid Esters of Ethylene Glycol | | | | | | | | | |
|---|---|---|---|---|---|---|---|---|---|---|
| | Initial | | | | $H_2O$ in the Condensate mmols | $H_2O$ Theoretical mmols | $H_2O$ Excess mmols | —OH Lost Meq. | —OH Free Meq. | B—O—B mmols |
| Run | $H_3BO_3$ mmols | $B_2O_3$ mmols | $(CH_2OH)_2$ mmols | Dioxane gm | | | | | | |
| A | 250.19 | 249.86 | 746.75 | 155.7 | 934.18 | 746.76 | 187.42 | 374.84 | 371.82 | 187.42 |
| B | 297.70 | — | 294.74 | 103.4 | 662.23 | 589.48 | 72.75 | 145.50 | 443.94 | 72.75 |
| C | 300.02 | — | 299.63 | 225.0 | 688.12 | 599.26 | 88.86 | 177.72 | 421.54 | 88.86 |

| | Initial | | | | Solution Weight gm | EGBE Weight gm | EGBE Solution % by wt. | —OH Free Meq./gm of solution | —OH Free Meq./gm of EGBE |
|---|---|---|---|---|---|---|---|---|---|
| Run | $H_3BO_3$ mmols | $B_2O_3$ mmols | $(CH_2OH)_2$ mmols | Dioxane gm | | | | | |
| A | 250.19 | 249.86 | 746.75 | 155.7 | 65.5 | 62.78 | 95.85 | 5.678 | 5.924 |
| B | 297.70 | — | 294.74 | 103.4 | 26.0 | 25.0 | 96.15 | 17.07 | 17.76 |
| C | 300.02 | — | 299.63 | 225.0 | 171.02 | 24.62 | 14.40 | 2.465 | 17.12 |

The data in Table I show that Runs B and C are not significantly different regardless of the amount of solvent used and of temperature in the distilling flask.

The use of $B_2O_3$, however, has a marked effect on the end product free —OH. Free —OH (meq./gm) in the product from Run A is significantly less than in the products of Runs B and C. This may be due to the possible presence of polymeric structures established through B—OH bonds which are more favored in Run A (due to the presence of $B_2O_3$ which carries B—O—B bonds) than in Runs B and C. The products from each Run have been characterized by IR spectroscopy in dioxane at 14% concentration level of EGBE.

No significant differences between each product may be detected from an IR spectra.

$HBO_2$ Preparation

Boric acid was heated at 175° C. for four hours. At 169° C., $H_3BO_3$ is dehydrated to $HBO_2$.

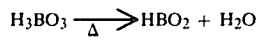

The weight loss of the sample of Run D corresponds to $H_2O$ loss analytically by taking up the residue with water after the heat treatment of 175° C. and determining the boric acid content. In this case the initial boric acid is recovered quantitatively, thus showing that the weight loss at 175° C. is only due to the water loss.

Run D was completed as follows:

19.9986 gm of $H_3BO_3$ (0.3234 mols) were heated at 175° C. for 4.5 hours. The weight loss was 6.3436 gm equivalent to 0.3524 mols of $H_2O$, which is 0.029 $H_2O$ mols in excess with respect to the stoichiometry of the dehydration reaction to $HBO_2$.

The $H_2O$ loss excess is attributed to $B_2O_3$ which is formed from further dehydration of $HBO_2$.

$$2HBO_2 \rightarrow B_2O_3 + H_2O$$

The composition of the dehydrated mixture of Run D was therefore:

| | |
|---|---|
| $B_2O_3$ | 0.029 (69.62) = 2.0190 gm |
| $HBO_2$ | 0.3234 − 2 (0.029) 43.84 = 11.6351 gm |
| Total mass = | 19.8986 − 6.3436 = 13.665 gm |
| Therefore | $HBO_2$ 85.21% |
| | $B_2O_3$ 14.79% |
| $HBO_2$ (mmols/gm) is $\frac{265.4}{13.665}$ = 19.42 | |

EXAMPLE 1

Adduct of EGBE and Methyl Isocyanate (MIC)

The reactor employed was a jacketed reactor equipped with a reflux condenser, thermometer and magnetic stirrer. 73.3 gm of the EBGE solution from Run C equivalent to 180.68 B—OH meq. and 159.86 MIC mmols (9.5 ml) equivalent to 88.5% of the starting B—OH were charged. The reflux condenser temperature was controlled at −3° C. with a cryostat to avoid MIC evaporation loss. The reaction temperature was increased by 10° C. each 30 minutes starting from 30° C. to a final temperature of 70° C. A precipitate forms at the beginning and increases with time and increased temperature.

IR spectra were made on samples taken each 30 minutes starting from the beginning of the reaction. The MIC 2280 $cm^{-1}$ band has disappeared at 70° C. The nujol IR spectrum of the isolated precipitate shows a band at 1710 $cm^{-1}$, which is characteristic of the adduct. The solid is hygroscopic and water soluble.

Storage of the solid in the absence of moisture at a temperature of 20° C. for two months did not affect its properties.

EXAMPLE 2

Release of Methyl Isocyanate

The adduct from Example 1 was slowly heated in a reactor equipped with a thermometer, a capillary ending tube to bubble nitrogen through the reaction mass, a jacketed Vigreux column with thermometer ending with a Claisen distillation head, a condenser and a tube to bubble the condensate in a jacketed graduated cylinder.

The decomposition reactor is heated with an oil bath. The Vigreux column is kept around 36° to 40° C. and the graduated cylinder for collection of the condensate distilling from the reaction mass is kept at 16° C. through circulation of running water.

This cylinder contains an absorbing solution of n-butylamine in dioxane. The volume and the titer of the butylamine solution is known. The absorption of methyl isocyanate by the amine occurs as follows:

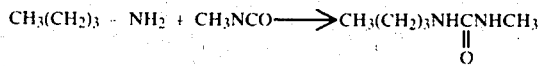

The reaction progress is followed by taking samples at different times and titrating the residual amine with HCl. No interference in this titration from the reaction product n-butyl-N'-methyl urea occurs. The reacted butylamine is equivalent to the amount of MIC formed during the decomposition reaction.

The reaction was run for one hour at 200° C. A substantially complete recovery of the methyl isocyanate was obtained.

EXAMPLE 3

Adduct of Metaboric Acid and Methyl Isocyanate (MIC)

77.75 mmols (4 gm of Run D contains 19.42 mmols/gm) of $HBO_2$ and 128 gm of sulfolane were charged in a 250 ml. three-necked flask equipped with a reflux condenser, thermometer and magnetic stirrer. The flask was heated one hour at 100° C. to dissolve most of $HBO_2$. Some undissolved $HBO_2$ appears after cooling to room temperature.

4.80 ml of MIC (77.75 mmols) were added and the solution was heated to 70° C. After two hours, the temperature was increased to 100° C. The reaction was stopped after five minutes at this temperature. At 70° C. some flocculant precipitate forms which was separated by centrifugation. The IR spectra relative to the supernatant liquid recovered after five minutes at 100° C. shows the absence of the MIC 2280 $cm^{-1}$ band, whereas the presence of the adduct is shown at a band at 1670 $cm^{-1}$.

The liquid adduct in sulfolane stored under anhydrous conditions at 20° C. remained unchanged over a period of two months.

EXAMPLE 4

Release of Methyl Isocyanate

The sulfolane solution of the adduct of Example 3 was heated according to the procedures and reactor of Example 2. The reaction was run for one hour at 200° C. and a substantially complete recovery of the methyl isocyanate was obtained.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An adduct of:
   (1) an isocyanate having the formula $$R-N=C=O$$

wherein R is a member selected from the group consisting of alkyl having from 1 to 10 carbon atoms and alkenyl having 2 to 6 carbon atoms with
   (2) a boron compound having at least one free =B—OH group selected from the group consisting of (a) polyol borates essentially free of alcoholic hydroxyl groups prepared from boric acid and polyols having at least two alcoholic hydroxyl groups selected from the group consisting of (i) compounds having the formula $$\begin{array}{c} R_1 \\ | \\ (CHOH)_m \\ | \\ (CH_2)_n \\ | \\ CHOH \\ | \\ R_1 \end{array}$$

wherein $R_1$ is a member selected from the group consisting of hydrogen, lower alkyl, and hydrocarbon aryl, n is 0 or an integer from 1 to 4, and m is 0 or an integer from 1 to 5, (ii) pentaerythritol, (iii) lower alkyl ethers of (i) or (ii), and (iv) lower alkanoic acid esters of (i) or (ii), and (b) metaboric acid.

2. The adduct of claim 1 wherein R is alkyl having from 1 to 4 carbon atoms.

3. The adduct of claim 1 wherein R is methyl.

4. The adduct of claims 1 or 3 wherein said boron compound is metaboric acid.

5. The adduct of claims 1 or 3 wherein said boron compound is polyol borate essentially free of alcoholic hydroxyl groups.

6. The adduct of claim 5 wherein said polyol borate essentially free of alcoholic hydroxyl groups is an ethylene glycol borate containing at least one free =B—OH group.

7. The adduct of claim 6 wherein said ethylene glycol borate has a ratio of ethylene glycol to boron of substantially 1:1.

8. The adduct of claims 1 or 3 wherein said adduct is a liquid to solid at temperatures below 100° C.

9. A process for the production of the adduct of claim 1 consisting essentially of reacting a carbonyl group containing compound selected from the group consisting of an isocyanate having the formula $$R-N=C=O$$

wherein R is a member selected from the group consisting of alkyl having from 1 to 10 carbon atoms and alkenyl having 2 to 6 carbon atoms, and a carbamoyl chloride having the formula $$R-NH-\overset{\overset{\displaystyle O}{\|}}{C}-Cl$$

wherein R has the above assigned values, with said boron compound having at least one free =B—OH group in a molar ratio of carbonyl group containing compound to =B—OH of 1:1 to 1:10.

10. The process of claim 9 wherein said carbonyl group-containing compound is said isocyanate.

11. The process of claim 10 wherein R is methyl.

12. The process of claim 9 wherein said carbonyl group-containing compound is said carbamoyl chloride and HCl is removed as a gas.

13. The process of claim 12 wherein R is methyl.

14. The process of claim 9 wherein said reaction is conducted at a temperature of from −5° C. to 125° C.

15. A process for storing and obtaining an isocyanate having the formula:

$$R-N=C=O$$

wherein R is a member selected from the group consisting of alkyl having from 1 to 10 carbon atoms and alkenyl having from 2 to 6 carbon atoms, consisting of the steps of reacting a carbonyl group containing compound selected from the group consisting of an isocyanate having the formula $$R-N=C=O$$

wherein R is a member selected from the group consisting of alkyl having from 1 to 10 carbon atoms and alkenyl having 2 to 6 carbon atoms, and a carbamoyl chloride having the formula $$R-NH-\overset{\overset{\displaystyle O}{\|}}{C}-Cl$$

wherein R has the above assigned values, with a boron compound having at least one free =B—OH group selected from the group consisting of (a) polyol borates essentially free of alcoholic hydroxyl groups prepared from boric acid and polyols having at least two alcoholic hydroxyl groups selected from the group consisting of (i) compounds having the formula $$\begin{array}{c} R_1 \\ | \\ (CHOH)_m \\ | \\ (CH_2)_n \\ | \\ CHOH \\ | \\ R_1 \end{array}$$

wherein $R_1$ is a member selected from the group consisting of hydrogen, lower alkyl, and hydrocarbon aryl, n is 0 or an integer from 1 to 4, and m is 0 or an integer from 1 to 5, (ii) pentaerythritol, (iii) lower alkyl ethers of (i) or (ii), and (iv) lower alkanoic acid esters of (i) or (ii), and (b) metaboric acid, either in the presence or absence of a solvent inert to isocyanate, to form an adduct, maintaining said adduct at temperatures below the decomposition temperature for the time desired, and heating said adduct to decompose the same with evolution of said isocyanate as a vapor.

16. The process of claim 15 wherein R is methyl.

17. The process of claims 15 or 16 wherein said heating step to decompose said adduct is conducted at a temperature of from 100° C. to 500° C.

18. The process of claims 15 or 16 wherein said heating step to decompose said adduct is conducted at a temperature of from 180° C. to 200° C.

19. The process of claims 15 or 16 wherein said reaction to form said adduct is conducted in a molar ratio of carbonyl group-containing compound to =B—OH of 1:1 to 1:10 in an organic solvent inert to said carbonyl group-containing compound, at a temperature above the freezing point of said solvent to below the decomposition point of said adduct.

20. The process of claim 9 or 10 or 11 wherein said reaction to form said adduct is conducted in a molar ratio of carbonyl group-containing compound to =B—OH of 1:1 to 1:10 in an organic solvent inert to said carbonyl group-containing compound, at a temperature above the freezing point of said solvent to below the decomposition point of said adduct.

* * * * *